United States Patent [19]
Toth

[11] Patent Number: 5,379,333
[45] Date of Patent: Jan. 3, 1995

[54] VARIABLE DOSE APPLICATION BY MODULATION OF X-RAY TUBE CURRENT DURING CT SCANNING

[75] Inventor: Thomas L. Toth, Brookfield, Wis.

[73] Assignee: General Electric Company, Milwaukee, Wis.

[21] Appl. No.: 155,037

[22] Filed: Nov. 19, 1993

[51] Int. Cl.⁶ .............................................. A61B 6/00
[52] U.S. Cl. ........................................ 378/16; 378/8; 378/108
[58] Field of Search .................. 378/4, 16, 8, 20, 109, 378/110, 108, 111, 112, 145, 146, 147, 150, 151

[56] References Cited

U.S. PATENT DOCUMENTS 4,624,007 11/1986 Muranushi ........................ 378/20 X
5,103,469 4/1992 Tanaka .................................. 378/16

OTHER PUBLICATIONS

U.S. patent application Ser. No. 854,227, filed May 19, 1986 and entitled "Dynamic Flux Intensity Control In Computer Tomography Systems".

*Primary Examiner*—David P. Porta
*Attorney, Agent, or Firm*—Quarles & Brady

[57] ABSTRACT

An x-ray CT system modulates x-ray tube current as a function of gantry angle to reduce the total patient dose without significantly increasing image noise. A scout scan is performed to acquire attenuation data which enables an optimal current modulation profile to be calculated for each slice in the scan.

9 Claims, 4 Drawing Sheets

FIG. 3
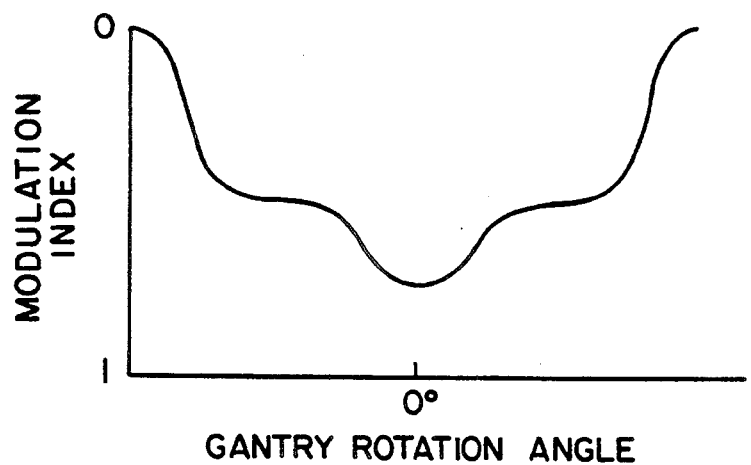
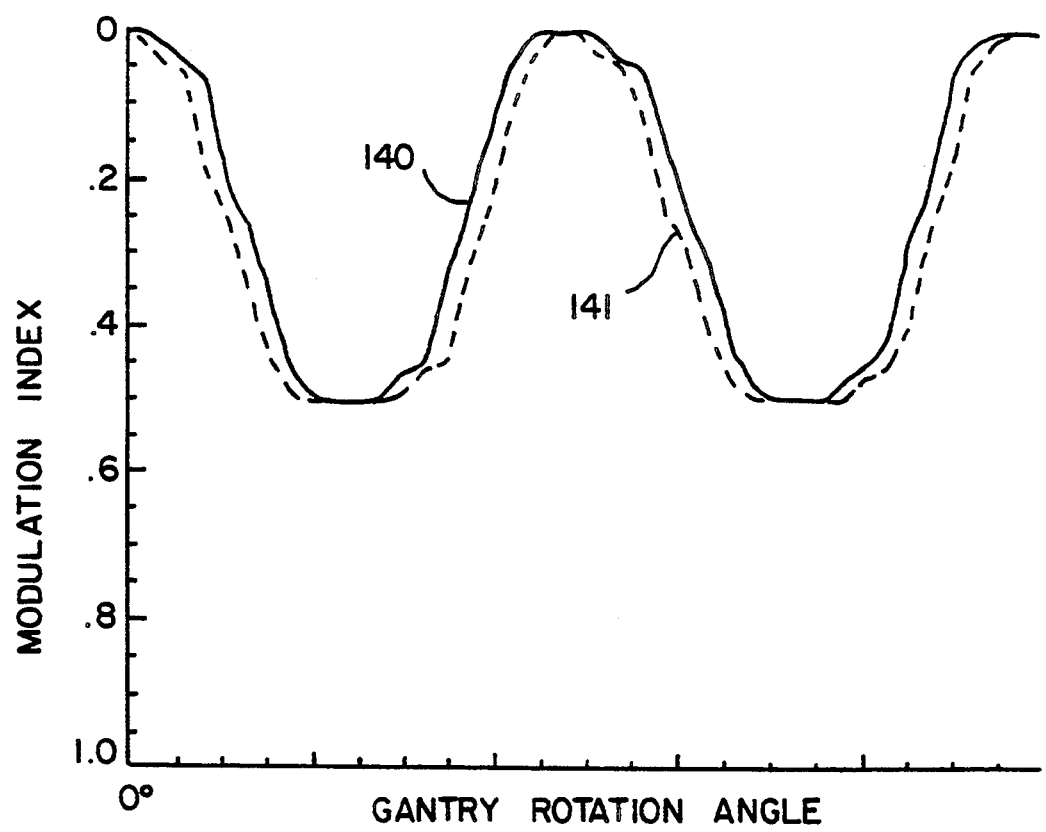
FIG. 4

VARIABLE DOSE APPLICATION BY MODULATION OF X-RAY TUBE CURRENT DURING CT SCANNING

BACKGROUND OF THE INVENTION

The present invention relates to computed tomography (CT) imaging apparatus; and more particularly, to reducing the x-ray dose applied to a patient without significantly increasing noise artifacts in the image.

In a computed tomography system, an x-ray source projects a fan-shaped beam which is collimated to lie within an X-Y plane of a Cartesian coordinate system, termed the "imaging plane." The x-ray beam passes through the object being imaged, such as a medical patient, and impinges upon an array of radiation detectors. The intensity of the transmitted radiation is dependent upon the attenuation of the x-ray beam by the object and each detector produces a separate electrical signal that is a measurement of the beam attenuation. The attenuation measurements from all the detectors are acquired separately to produce the transmission profile.

The source and detector array in a conventional CT system are rotated on a gantry within the imaging plane and around the object so that the angle at which the x-ray beam intersects the object constantly changes. A group of x-ray attenuation measurements from the detector array at a given angle is referred to as a "view" and a "scan" of the object comprises a set of views made at different angular orientations during one revolution of the x-ray source and detector. In a 2D scan, data is processed to construct an image that corresponds to a two dimensional slice taken through the object. The prevailing method for reconstructing an image from 2D data is referred to in the art as the filtered backprojection technique. This process converts the attenuation measurements from a scan into integers called "CT numbers" or "Hounsfield units", which are used to control the brightness of a corresponding pixel on a cathode ray tube display.

Quantum noise degrades the diagnostic quality of a CT image and this noise is related to the amount of x-rays, or "dose", employed to acquire the attenuation measurements, and to the attenuation characteristics of the patient. Image artifacts due to noise will increase if the x-rays measured at the detector drop to low levels either because the prescribed x-ray dose is too low or the beam is highly attenuated by patient anatomy. The x-ray dose is controlled by the filament current ("mA") applied to the x-ray tube, and the practice is to fix this current at a level which provides a constant dose during the entire scan. If the operator prescribes a high dose, image quality is superb throughout, but excessive x-ray flux is produced during portions of the scan when patient attenuation is low. The patient is thus exposed to an excessive dose and the x-ray tube is unnecessarily heated. On the other hand, if the dose is reduced (to prevent tube overheating during the prescribed scan), noise artifacts will appear in the image oriented at locations where the beam is highly attenuated. For example, horizontal streaks may appear in slices through a patient's shoulders and hips.

SUMMARY OF THE INVENTION

The present invention relates to a CT imaging system in which the x-ray dose is modulated as the gantry is rotated during a scan such that a prescribed noise level is better maintained in all of the acquired attenuation measurements. More specifically, a modulation profile which is indicative of the variations in patient attenuation during a revolution of the gantry is employed during the scan to modulate x-ray tube current as a function of gantry rotation to dynamically scale the dose as required by the patient's anatomy. In one implementation, a modulation profile is stored for imaging specific human anatomy (such as the eyes), and in another implementation the modulation profile is constructed from a general purpose modulation template which is "tailored" to the patient's particular anatomy using attenuation data acquired with a "scout" scan.

A general object of the invention is to minimize the x-ray dose applied to a patient while maintaining a prescribed small noise increase in the reconstructed image. The values in the modulation profile reflect the expected attenuation of the x-ray beam at all gantry angles, and they modulate the tube current (mA) such that attenuation measurements are obtained at a desired noise level throughout the scan. As a result, the dose may be substantially reduced at some gantry angles where patient attenuation is low. For example, consider a scan through the patient's hips where the dose is kept constant for a horizontal view (highly attenuated) and a vertical view (low attenuation). If the noise figure for the highly attenuated view is 10, the noise figure for the other view may only be 1. A characteristic of CT is that these noise figures add as the square root of the sum of the squares (i.e. $(10^2+1^2)^{\frac{1}{2}}$), such that the low noise view contributes minimally to the total noise figure and to image artifacts. This is why image artifacts typically appear as streaks in the direction of the highly attenuated views. Doubling the smaller noise figure in this example by substantially cutting the x-ray dose at vertical gantry positions only increases the total noise by 1.5%. Since noise increases of less than 5% generally cannot be seen in the reconstructed image by radiologists, this affords ample opportunity to reduce x-ray dose over a wide range of gantry angles at many slice locations.

Another object of the invention is to reduce the x-ray exposure of specific portions of the patient without significantly increasing image noise. Some organs, such as the eyes, are particularly sensitive to ionizing radiation. By modulating the beam intensity as a function of gantry angle such that the dose is reduced at the gantry angles in which the eyes are directly exposed to the x-ray source, the total dose to the eyes is reduced. To maintain noise within prescribed limits, the beam intensity is increased for opposing views in which the x-ray source is rotated behind the patient's head. The modulation profile for such a scan is shown in FIG. 3.

Another object of the invention is to automatically generate a modulation profile for use in scanning a patient with minimal dose and a clinically insignificant noise increase. A transverse slice through a patient may be viewed radiologically as an oval shape having major and minor axes which change along the length of the patient. For example, at the hips the major axis is horizontal and muck longer than the vertical minor axis, whereas at the neck, the major axis is vertical and only a little longer than the minor axis. At other locations the radiological profile may be nearly circular. A general purpose modulation template having a substantially sinusoidal shape at twice the frequency of the gantry rotation may be automatically tailored to such radiological profiles by acquiring two orthogonal views through the transverse slice prior to the scan. This "patient projection" data is analyzed to locate the major and minor axes of the oval and determine their relative lengths. This information is employed to produce a modulation profile from the sinusoidal template. Such a modulation profile is shown in FIG. 4 for a slice having a horizontal major axis substantially greater than a vertical minor axis. This will reduce tube current (mA) to 50% of its prescribed amount as the x-ray source rotates above and below the patient. For a slice with less difference between the major and minor axes, the tube current would be reduced by less than 50%.

A more specific object of the invention is to alter the shape of the modulation profile when the x-ray source cannot be modulated enough to reduce the dose. The ability of the x-ray tube and its filament current supply to respond to the modulation profile may be limited. For example, a 50% modulation may be the limit. It is a teaching of the present invention that the shape of the modulation profile can be changed when the modulation limit is exceeded to recapture some benefit of the desired lower dose level.

BRIEF DESCRIPTION OF THE DRAWINGS

FIG. 3 is a graphic representation of a modulation profile for scanning a patient's head with reduced x-ray dose to the eyes;

FIG. 4 is a graphic representation of a sinusoidal modulation profile employed in the preferred embodiment of the invention;

DETAILED DESCRIPTION OF THE INVENTION

Figure 1:
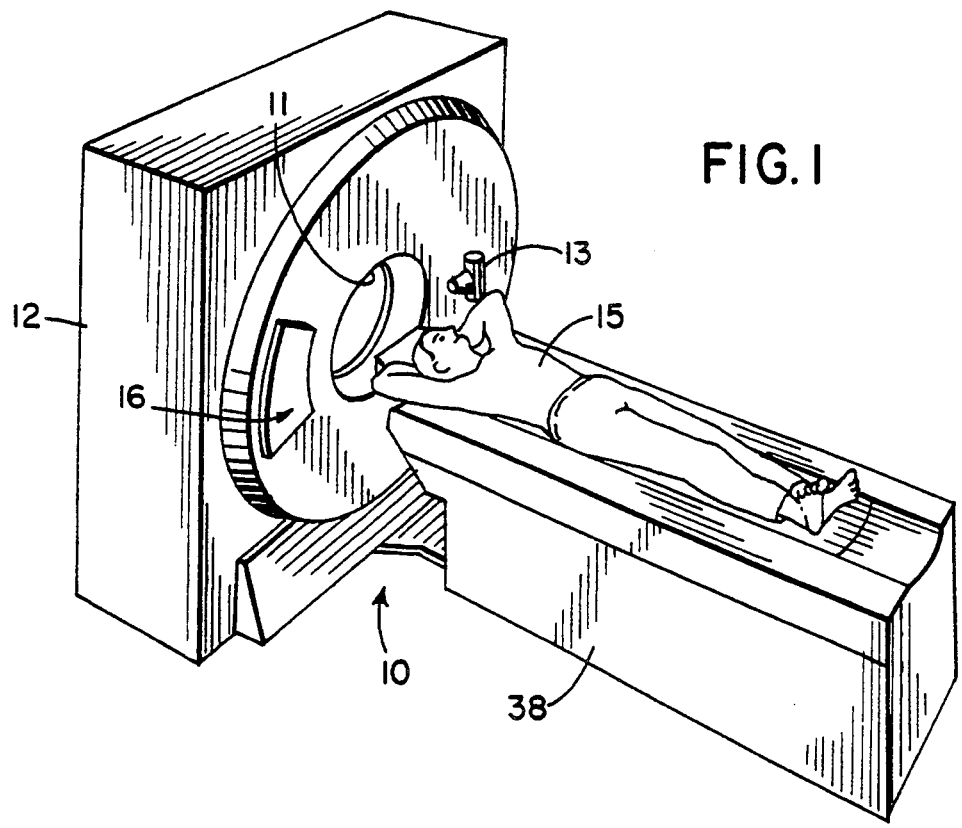
FIG. 1 is a pictorial view of a CT imaging system in which the present invention may be employed.
Figure 2:
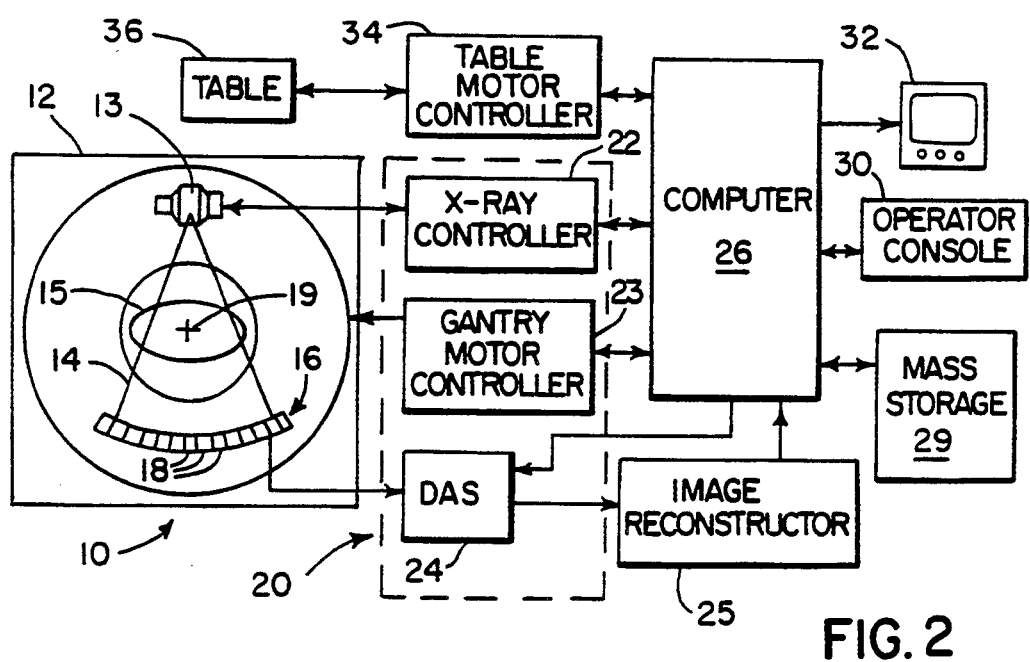
FIG. 2 is a block schematic diagram of the CT imaging system.

With initial reference to FIGS. 1 and 2, a computed tomography (CT) imaging system 10 includes a gantry 12 representative of a "third generation" CT scanner. Gantry 12 has an x-ray source 13 that projects a beam of x-rays 14 toward a detector array 16 on the opposite side of the gantry. The detector array 16 is formed by a number of detector elements 18 which together sense the projected x-rays that pass through a medical patient 15. Each detector element 18 produces an electrical signal that represents the intensity of an impinging x-ray beam and hence the attenuation of the beam as it passes through the patient. During a scan to acquire x-ray projection data, the gantry 12 and the components mounted thereon rotate about a center of rotation 19 located within the patient 15. A reference detector at one end of the array 16 measures the unattenuated beam intensity during the scan to detect variations in the applied x-ray dose. This reference data is used in subsequent processing of the x-ray projection data to normalize it to a common reference dose.

The rotation of the gantry and the operation of the x-ray source 13 are governed by a control mechanism 20 of the CT system. The control mechanism 20 includes an x-ray controller 22 that provides power and timing signals to the x-ray source 13 and a gantry motor controller 23 that controls the rotational speed and position of the gantry 12. A data acquisition system (DAS) 24 in the control mechanism 20 samples analog data from detector elements 18 and converts the data to digital signals for subsequent processing. An image reconstructor 25, receives sampled and digitized x-ray data from the DAS 24 and performs high speed image reconstruction. The reconstructed image is applied as an input to a computer 26 which stores the image in a mass storage device 29.

The computer 26 also receives con, hands and scanning parameters from an operator via console 30 that has a keyboard. An associated cathode ray tube display 32 allows the operator to observe the reconstructed image and other data from the computer 26. The operator supplied commands and parameters are used by the computer 26 to provide control signals and information to the DAS 24, the x-ray controller 22 and the gantry motor controller 23. In addition, computes 26 operates a table motor controller 34 which controls a motorized table 36 to position the patient 15 in the gantry 12.

Figure 5:
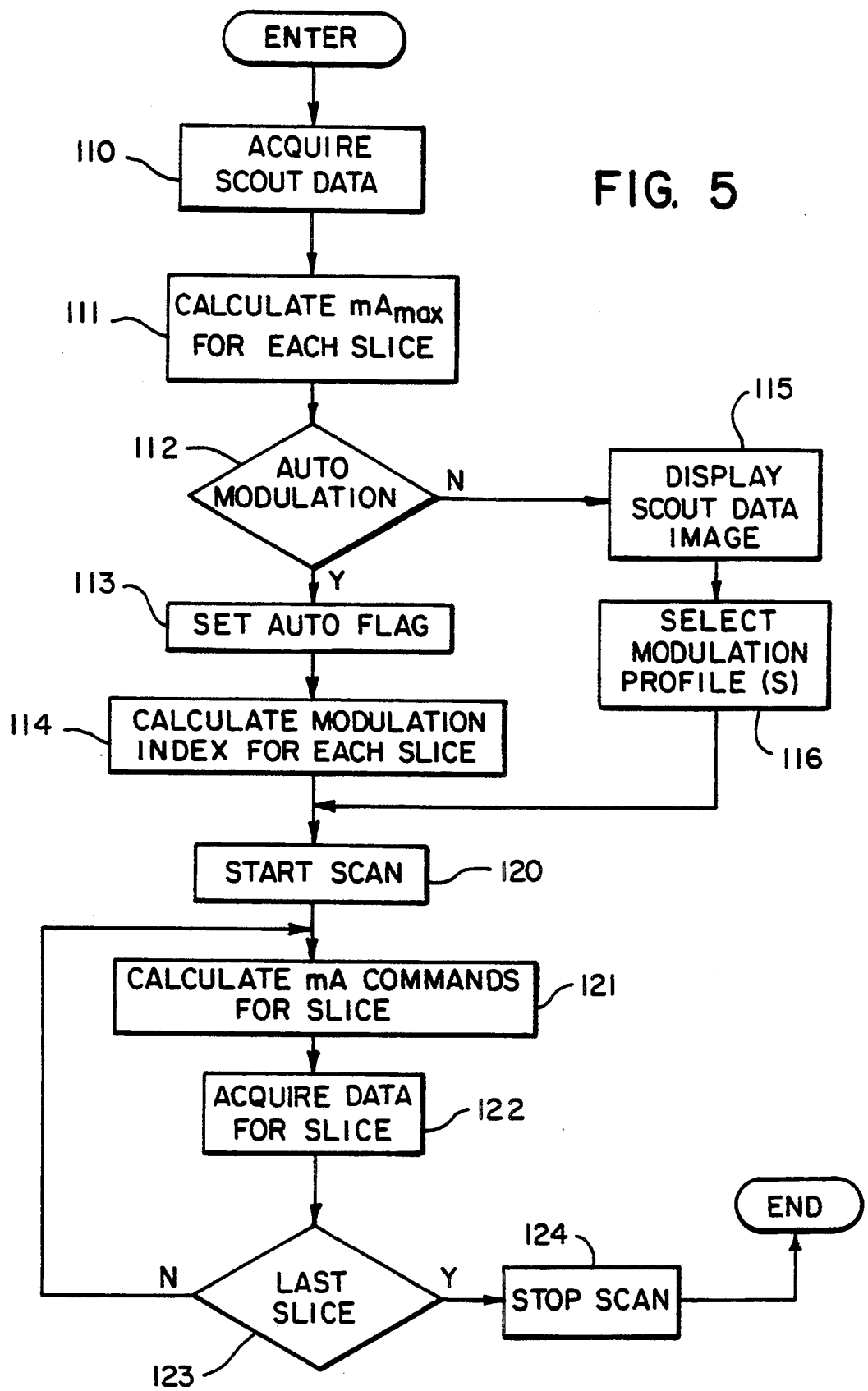
FIG. 5 is a flow chart of a program executed by the CT imaging system of FIG. 2 to carry out the preferred embodiment of the invention.

Referring particularly to FIG. 2, the computer 26 directs the system components to carry out the prescribed scan in accordance with stored programs. If an mA modulation strategy is selected by the operator, the program illustrated by the flow chart in FIG. 5 is executed by computer 26 to implement the preferred embodiment of the present invention. The first step is to acquire scout data, as indicated at process block 110. This scout data is comprised of two orthogonal views from each slice in the prescribed scan, one at a gantry angle of 0° and the other at an angle of 90°. The next step, as indicated at process block 111, is to calculate the maximum x-ray tube current ($mA_{max}$) for each slice using the scout data as described in copending U.S. patent application Ser. No. 08/155,045 filed on even data herewith and entitled "Dynamic Dose Control In Multi-Slice CT Scan." This enables the x-ray dose to be reduced for slices with reduced attenuation of the x-ray beam without exceeding the prescribed image noise. It results in an array of stored values ($mA_{max}$), one for each of the respective slices in the scan.

As indicated at decision block 112, the operator is then signalled to indicate if automatic modulation is to be applied during the scan, and if so, a flag is set at process block 113 and a modulation index ($\alpha$) is calculated for each slice as indicated at process block 114. As described in detail below, the modulation index ($\alpha$) is calculated from the scout data and it indicates the degree to which x-ray tube current can be modulated without significantly increasing noise artifacts in the reconstructed image. This modulation index is used to produce a modulation profile as will also be described below.

If the automatic mode is not selected, the system branches at decision block 112 and the scout data is employed to produce an image for the operator at process block 115. This image enables the operator to locate the prescribed slices with respect to the patient's anatomy and to manually select appropriate x-ray tube current modulation profiles at process block 116. For example, the operator may choose special purpose modulation profiles such as that shown in FIG. 3 for those slices intersecting the patient's eyes. This particular profile reduces tube current while the x-ray tube is above the patient to thereby reduce the x-ray dose applied directly to the eyes. To compensate for this lower dose without increasing image noise, the x-ray tube current is increased above the prescribed amount when the gantry revolves the x-ray source to the back of the patient's head. In the preferred embodiment, this and other modulation profiles are stored as twenty values which, when multiplied by the maximum tube current ($mA_{max}$) calculated above, provide twenty current commands for the x-ray controller 22 that determine x-ray tube current at twenty successive 18° segments of gantry revolution.

Referring still to FIGS. 2 and 5, regardless of the modulation profile selected, the computer 26 starts the scan at process block 120, by signaling the gantry motor controller 23. It then enters a loop in which the twenty mA commands are calculated at process block 121 and downloaded to the x-ray controller 22. When the auto mode has been selected, this step involves the application of the modulation index ($\alpha$) calculated above and the maximum current ($mA_{max}$) also calculated above to a general purpose sinusoidal template expressed as follows:

$$mA = mA_{max}\left[\left(1 - \frac{\alpha}{2}\right) - \frac{\alpha}{2}\cos(2wt + \phi)\right] \quad (1)$$

where:
$mA_{max}$ = the tube current without modulation,
$\alpha$ = modulation index calculated from the scout data;
$wt$ = gantry angle ($\theta$) at time t, and
$\phi$ = starting phase in the sinusoidal template determined from the scout data.

In the manual mode, the calculation of the twenty mA commands requires multiplication of the maximum current ($mA_{max}$) by the twenty stored modulation profile values. Regardless of the mode, at process block 122 the twenty mA values are downloaded to the x-ray controller 22 and a timing signal is sent to coordinate the start of the dose with gantry orientation and table position.

As each slice is acquired the gantry 12 is rotated at a constant angular rate by the gantry motor controller 23. At the completion of each 18° increment of gantry rotation the next mA current command downloaded to the x-ray controller 22 is read out and used to control x-ray tube filament current during the next 18° increment of rotation. This cycle continues until all twenty mA current commands have been applied in succession as the gantry completes a 360° rotation.

The cycle of calculating mA current commands and downloading them to the x-ray controller 22 continues until the last slice in the prescribed scan is acquired as detected at decision block 123. The gantry is then stopped at process block 124 and the operator is signaled that the scan is finished.

The acquired x-ray profile data is processed in the usual fashion to reconstruct a slice image. Even though the views are acquired with varying x-ray beam intensity, the data is normalized with the reference detector signal as mentioned above so that the reconstruction of the image is performed with x-ray profile data that is effectively acquired with a constant x-ray beam intensity during the entire gantry revolution.

The acquisition of scout data is required to implement the automatic dose modulation mode described above. To accomplish this, the patient table 36 is moved and the gantry is rotated to acquire attenuation data for two orthogonal views in each slice to be imaged. In the preferred embodiment, gantry angles of 0° and 90° are chosen for the scout data:

$$S_0(i,z) \text{ and } S_{90}(i,z)$$

where:
i = detector channel number; and
z = location of slice along z axis.

Figure 6A:
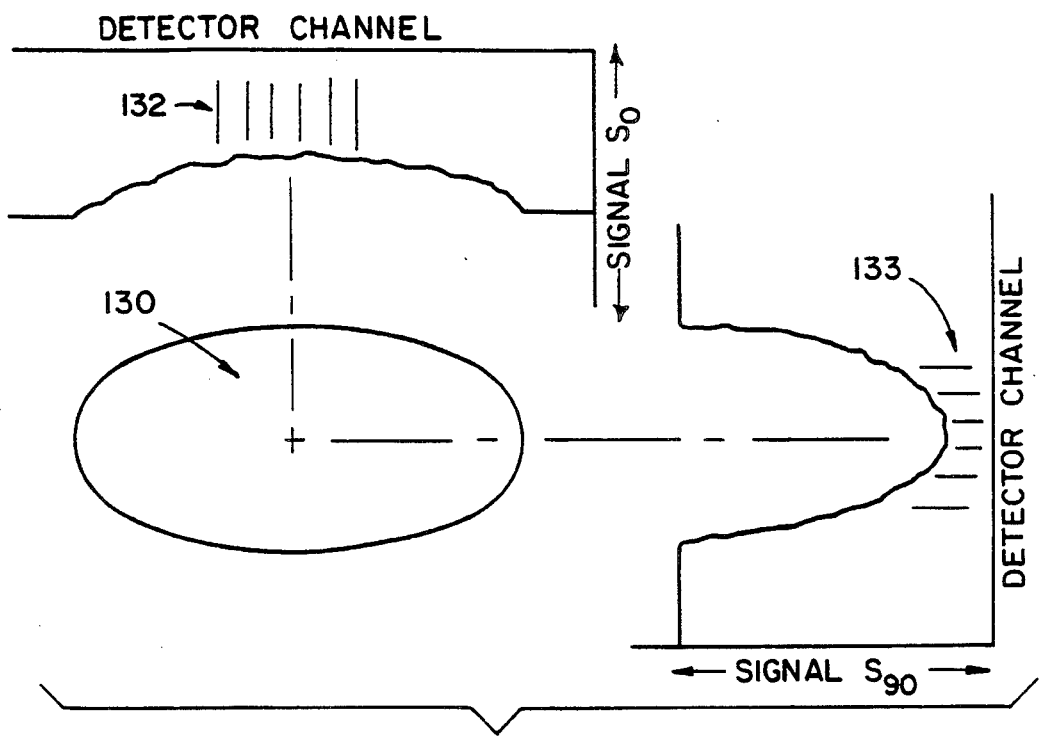
FIGS. 6A and 6B are schematic representations of exemplary scout data acquired at two locations in a patient.
Figure 6B:
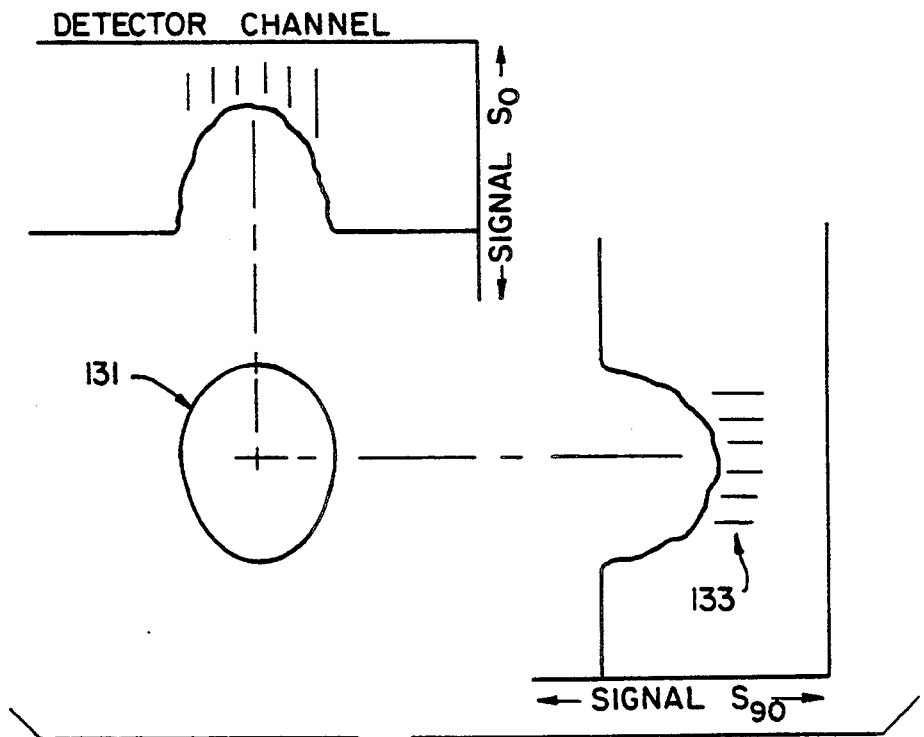

As shown in FIG. 6A, when the slice intersects the patient's shoulders the signal $S_0(i,z)$ is attenuated very much less than the signal $S_{90}(i,z)$ because the attenuation profile 130 at this point in the human anatomy is much wider than it is high. As shown in FIG. 6B, however, when the scout slice intersects the patient's neck the signal $S_0(i,z)$ is attenuated more than the signal $S_{90}(i,z)$ because the attenuation profile 131 is narrower than it is high. The scout data is analyzed to detect these differences in attenuation profiles so that the values of $\alpha$ and $\phi$ required by the general purpose sinusoidal template described above in equation (1) may be calculated. These are determined from the scout data as follows. First, offset corrections are made to each channel (i) of the raw data received from the DAS 24.

$$S_0(i,z) = S_0(i,z) - \text{offsets}(i)$$

$$S_{90}(i,z) = S_{90}(i,z) - \text{offsets}(i)$$

This corrected data is then convolved along the z axis with a 10 point low pass filter $F(z)$ and the filtered data is resampled at each 5 mm slice in the scan. The filtered scout data in each slice is then low pass filtered in i by finding the average value in each of five 70 channel regions centered on the isocenter. These five central regions are indicated at 132 and 133 in FIG. 6A. For each slice the minimum average value $\min_0(z)$ from the five 0° regions and the minimum average value $\min_{90}(z)$ from the five 90° regions are found. The modulation index $\alpha$ and phase $\phi$ are a function of the patient attenuation ratio and are calculated as follows:

$$\text{if } \min_0(z) > \min_{90}(z), \text{ then } \alpha = f\left[\frac{\min_0(z)}{\min_{90}(z)}\right] \phi = 0$$

$$\text{if } \min_0(z) < \min_{90}(z) \; \alpha = f\left[\frac{\min_{90}(z)}{\min_0(z)}\right] \phi = \pi.$$

A table of modulation indices ($\alpha$) vs attenuation ratios can be generated empirically to produce a small known amount of noise increase in the image (i.e., 5%). As the patient attenuation ratio increases, the image noise decreases, and thus the % modulation can be increased to further decrease patient dose without exceeding the 5% image noise limit. The table is fixed and need be computed only once and is provided as part of the system software. In the preferred embodiment of the invention a table with the following eight entries is used.

| ratio | $\alpha$ |
| --- | --- |
| 1.0 | 0.0 |
| 1.5 | .1 |
| 2.9 | .2 |
| 6.3 | .25 |
| 14.9 | .33 |
| 28.7 | .44 |
| 60 | .60 |

| ratio | α |
|---|---|
| 133 | .75 |

During patient scanning, the attenuation ratio determines the index into this table (which can be linearly interpolated between entries) to produce the proper modulation index ($\alpha$).

These values are employed in equation (1) above to calculate the twenty current commands (mA) at successive 18° (i.e. $2\pi/20$ radians) gantry angles ($\theta$) which comprise the modulation profile. Such a modulation profile is illustrated by the solid line 140 in FIG. 4, where the modulation index ($\alpha$) is approximately 0.5. For slices passing through patient attenuation profiles that are more circular, the value of $\alpha$ is less and the sinusoidal modulation of the current commands mA in FIG. 4 are reduced. On the other hand, when the measured patient attenuation profile becomes very oblong, the modulation index ($\alpha$) becomes larger and the sinusoidal modulation of the current commands mA becomes greater.

At some point, it may not be possible to further increase modulation to achieve further dose reduction because of limitations inherent in the X-ray tube and generator. If the dose cannot be modulated by the full amount indicated by the scout data, the shape of the sinusoidal template can be changed to realize at least a portion of the dose savings. This is illustrated by the dashed line 141 in FIG. 4 for the situation in which a modulation index greater than 0.5 cannot be achieved and the template shape is changed to increase the width of the low mA duty cycle.

The patient attenuation ratio is predetermined at the point where the dashed waveform 141 in FIG. 4, with a 0.5 modulation index, produces a 5% image noise increase. This occurs at a higher patient attenuation ratio than for the solid waveform 140 in FIG. 4. Between the attenuation ratios for maximum modulation of the solid waveform 140 and the dashed waveform 141, the waveform shape is linearly interpolated. Thus, the dose savings can be increased beyond the solid waveform 140 to the maximum provided by the dashed waveform 141. The dashed waveform 141 would not be used for lower attenuation ratios since it is less efficient and would produce higher patient dose for the same image noise increase than the solid waveform 140 at these attenuation ratios.

It should be apparent to those skilled in the art that many modifications can be made to the preferred embodiment described herein without departing from the spirit of the invention. For example, other preset modulation profiles may be stored and presented to the operator for use during the scan. Also, while the sinusoidal shape at twice the gantry frequency is preferred as the general purpose template, other shapes are possible. Also, while the patient projection data is obtained in a scout scan in which views are acquired at gantry angles of 0° and 90° in the preferred embodiment, different angles can be used and more scout views can be acquired to gather the patient attenuation profile information. Also, the patient projection data may be acquired in a helical survey scan or from an adjacent slice which has already been acquired. It should also be apparent that the present invention is applicable to a CT system which acquires each slice either while the patient table is stationary or in a spiral scan in which the table is moved continuously throughout the data acquisition.

I claim:

1. A method for reducing the dose of an x-ray beam applied to a patient by an x-ray CT system during the acquisition of attenuation data from a single slice as a gantry rotates around the patient, the steps comprising:
   acquiring patient projection data from the slice which indicates patient attenuation of the x-ray beam at two substantially orthogonal gantry angles;
   calculating a modulation profile using information derived from the acquired patient projection data, the modulation profile indicating the x-ray dose to be applied to the patient as a function of gantry angle; and
   acquiring the attenuation data for the single slice by rotating the gantry around the patient and modulating the applied x-ray dose as indicated by the modulation profile.

2. The method as recited in claim 1 in which the x-ray dose is modulated by changing the current supplied to the x-ray tube.

3. The method as recited in claim 1 in which the modulation profile varies the x-ray dose substantially sinusoidally as a function of gantry angle, and the info,-nation derived from the patient projection data is a modulation index which indicates the magnitude of the variations.

4. The method as recited in claim 3 in which the modulation index is derived by calculating the ratio of patient projection data acquired at said two substantially orthogonal gantry angles.

5. The method as recited in claim 3 in which the shape of the modulation profile is changed when the modulation index exceeds a preset amount.

6. The method as recited in claim 3 in which the modulation index is derived by calculating the ratio of patient projection data acquired at said two substantially orthogonal gantry angles and using said ratio to read the modulation index from a table storing a plurality of different modulation indices.

7. A method for reducing the dose of an x-ray beam applied to a patient by an x-ray CT system during the acquisition of attenuation data from a single slice, the steps comprising:
   storing a modulation profile which indicates variations in x-ray beam intensity as a function of gantry angle during the acquisition of attenuation data;
   modulating an x-ray tube operating parameter using values stored in the modulation profile; and
   acquiring a slice of attenuation data while the x-ray tube operating parameter is modulated.

8. The method as recited in claim 7 in which the x-ray tube operating parameter is tube current.

9. The method as recited in claim 7 in which the modulation profile is shaped to reduce the x-ray dose while the gantry is oriented to position the x-ray tube directly over the patient's eyes, and to increase the x-ray dose when the x-ray tube is positioned directly over the back of the patient's head.

* * * * *